United States Patent [19]

Faccioli et al.

[11] Patent Number: 5,281,224
[45] Date of Patent: Jan. 25, 1994

[54] CENTERING MEANS FOR HOLES OF INTRAMEDULLARY NAILS

[75] Inventors: Giovanni Faccioli, Mantovia; Stefano Rossi, Verona, both of Italy

[73] Assignee: Orthofix S.r.l., Bussolengo, Italy

[21] Appl. No.: 618

[22] Filed: Jan. 5, 1993

[51] Int. Cl.⁵ ............................................. A61B 17/56
[52] U.S. Cl. .......................................... 606/62; 606/67
[58] Field of Search ................................... 606/61–68, 606/96, 97, 98, 86, 87, 88

[56] References Cited

U.S. PATENT DOCUMENTS

| | | | |
|---|---|---|---|
| 2,812,761 | 11/1957 | Palkovitz | 606/64 |
| 4,621,628 | 11/1986 | Brudermann | 606/64 |
| 4,667,664 | 5/1987 | Taylor | 606/64 |
| 4,881,535 | 11/1989 | Sohngen | 606/64 |
| 4,911,153 | 3/1990 | Border | 606/64 |
| 4,913,137 | 4/1990 | Azer | 606/64 |
| 5,127,913 | 7/1992 | Thomas | 606/62 |

*Primary Examiner*—Michael A. Brown
*Attorney, Agent, or Firm*—Hopgood, Calimafde, Kalil, Blaustein & Judlowe

[57] ABSTRACT

A jig is detachably secured to the proximal end of an installed intramedullary nail having a transverse bolt hole near the distal end of the nail. The jig comprises an offsetting arm which so mounts an elongate template as to be movable in a geometric plane substantially parallel to the nail. A guide bore near the distal end of the template is on an axis perpendicular to the geometric plane. When the jig is chucked to the nail, the axis of the guide bore of the template is parallel to the axis of the bolt hole of the nail, and both the guide-bore axis and the bolt-hole axis are at identical distance from the offsetting arm. The distal end of the template is adapted to removably mount a metal-detector establishing a magnetic-field about a directional axis, such that the metal-detector can be selectively moved or positioned on one and then the other side of a central position in which the template is strictly parallel to the nail. Template positions noted for equal detector signals on opposite sides of the central position enable determination of the central position and therefore the location at which the template guide bore is in axial alignment with the bolt hole of the nail.

15 Claims, 5 Drawing Sheets

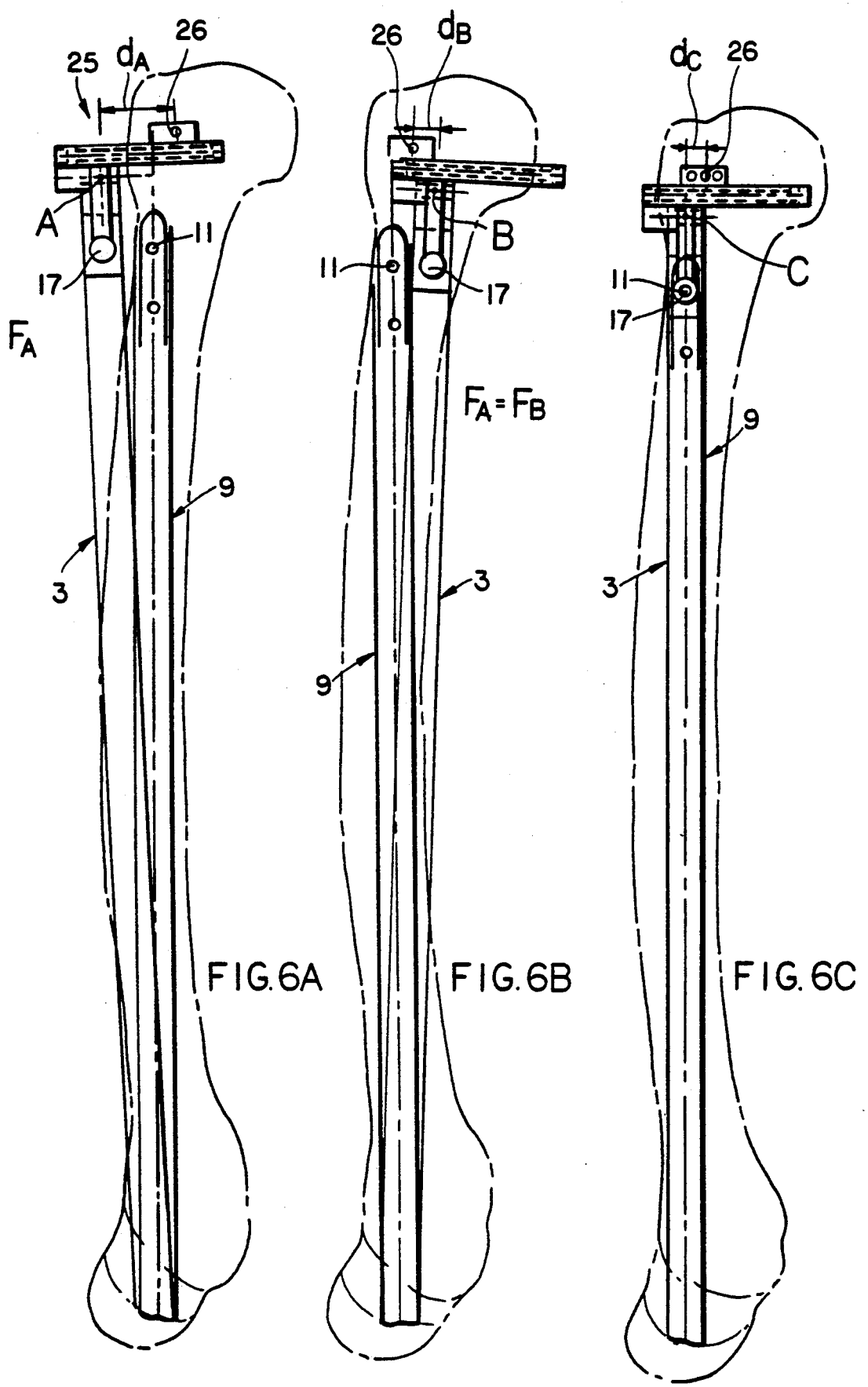

CENTERING MEANS FOR HOLES OF INTRAMEDULLARY NAILS

BACKGROUND OF THE INVENTION

This invention relates to centering means for holes of intramedullary nails, of the type used in bone surgery.

For the surgical repair and stabilization of fractures of long bones, such as the femur, tibia, humerus and fibula, it has long been known to insert an intramedullary nail of appropriate length into the medullary cavity, and to anchor bone fragments to the nail. Anchorage is achieved by means of bolts or pins which are screwed into the walls of the bone on opposite sides of the medullary cavity, and these bolts or pins pass through transverse holes located in the vicinity of the proximal and distal ends of the intramedullary nail. The anchoring bolts are held in position until confronting edges of the broken bone have completely grown back, and are then extracted to allow the intramedullary nail to be removed. The procedure for inserting the bolts requires (a) accurate location of the transverse holes in the intramedullary nail, (b) drilling through the cortical and spongy tissue of the bone to provide passages for the bolts, and (c) inserting bolts in such a way as to secure the nail in a suitable position with respect to the bone fragments.

The most critical part of this procedure is to determine, from outside, the location and center of so-called blind holes in the nail; this must be done with the maximum possible accuracy in order to avoid any misalignment of drilled holes and repeated drilling of the bone.

The known method of centering provides for the use of a drilling mask or frame consisting of a longitudinal template which can be attached to the intramedullary nail at its proximal end and which is provided with holes to house bushes for drilling the bone at positions aligned with the holes in the nail.

The centering of holes toward the proximal end of the intramedullary nail, close to the area of attachment to the frame, is a relatively simple operation which does not give rise to any special problems. On the other hand, the centering of blind holes near the distal end of the intramedullary nail is very much more difficult because of the elasticity of the template, and play in the vicinity of coupling between the frame and the intramedullary nail.

A great many centering devices have been proposed, using orientable drilling bushes or a more rigid drilling template with less play in the frame/nail coupling. However, none of these proposed arrangements have been sufficiently rigid; as a result, these proposed arrangements do not ensure the accuracy which is needed for repeatable precision drilling at the distal end of the nail.

It should also be noted that all the known centering devices mentioned above require an X-ray source, which is used by the surgeon to check the hole location with respect to the outer surface of the patient's limb.

The known techniques are hazardous because they require the patient and healthcare personnel surrounding him to suffer repeated and prolonged exposure to X-rays, which are well known to be harmful beyond certain limits, but which cannot be switched off without compromising the final result of an operation. Also, X-rays cannot be used to accurately establish the axial orientation of a hole with respect to the external surface of the limb because the X-ray image is projected onto a plane and cannot be used for a clear determination of any errors in the inclination of the hole.

U.S. Pat. No. 4,667,664 discloses a centering device for the blind holes of an intramedullary nail, wherein a bar supports an X-ray aiming device at one end and the intramedullary nail at the other end; the device is provided with a stabilizing member comprising an arm which connects a median portion of the bar to an intermediate point, between the proximal and distal ends of the nail. But even this device is not sufficiently stable with respect to the distal end of the nail, and therefore the device does not offer maximum assurance of accuracy and stability in the drilling of bone at a distal location. Also, this device again makes use of X-rays, and is therefore unreliable and unsafe.

BRIEF STATEMENT OF THE INVENTION

The principal object of this invention is to overcome the above-mentioned disadvantages by providing a hole-centering device and technique which offers high reliability and accuracy, without requiring the use of X-rays.

Another object is to meet the above object with a device and technique of extreme simplicity and accuracy.

The invention achieves these objects, for the case of an intramedullary nail having proximal and distal ends, with plural transverse holes close to these ends, by providing a frame for supporting transverse bolts from outside the involved limb. The frame comprises a longitudinal template having transverse guide bores for drilling tools, and these guide bores are spaced to accord with the spacing of the transverse holes of the intramedullary nail. The frame further comprises at its proximal end a transverse arm for removable attachment of the proximal end of the nail, such that the template is parallel to the nail, with template bores at approximately equal offset from and potential alignment with holes of the nail. At the distal end of the frame, provision is made for limited displacement of the frame in a plane that is substantially perpendicular to the transverse holes and bores, and such limited displacement is guided by a stabilizing member which can be anchored to the distal bone fragment that contains the distal end of the intramedullary pin, the anchorage being distally beyond the distal end of the intramedullary nail. Preferably, the stabilizing member includes a bar that is threaded for screwed anchorage to the bone, in the proximity of a distal metaphysis, such that the axis of the bar is substantially perpendicular to the axis of the bone. A metal-detecting instrument carried by the frame is capable of detecting the location of a blind hole in the intramedullary nail, in the course of stabilized and guided displacement of the distal end of the frame; when this instrument detects alignment of the guide bore with the blind hole, the distal end of the frame is clamped to the stabilizing member, and guided drilling can proceed.

DETAILED DESCRIPTION OF THE INVENTION

The invention will be described in detail, for a preferred embodiment, in conjunction with the accompanying drawings, in which:

FIGS. 6a, 6b, and 6c diagrammatically illustrate three successive stages in a procedure for using the device of the invention.

Figure 1:
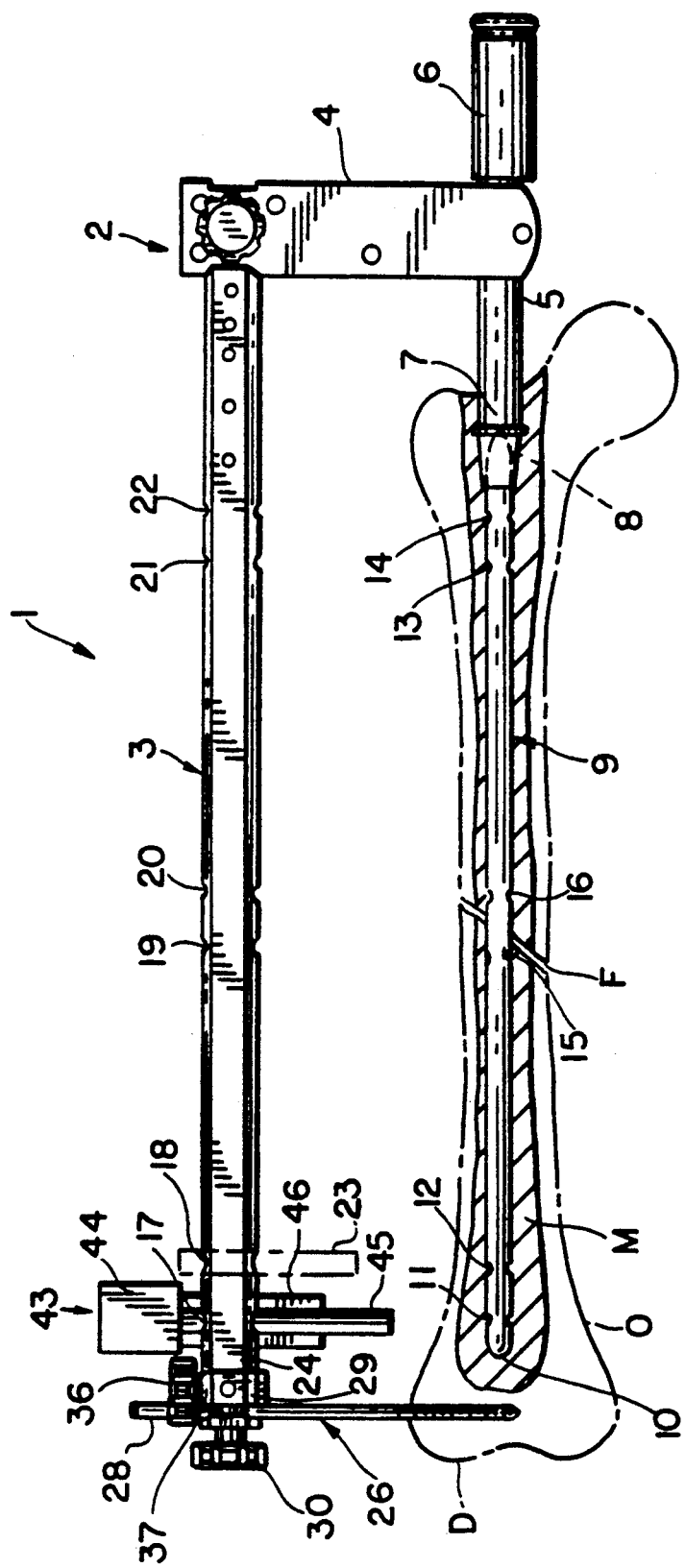
FIG. 1 is a side elevation of a device of the invention, namely, centering means for an intramedullary nail, shown in application to a bone having a fracture between distal and proximal fragments of the bone.
Figure 2:
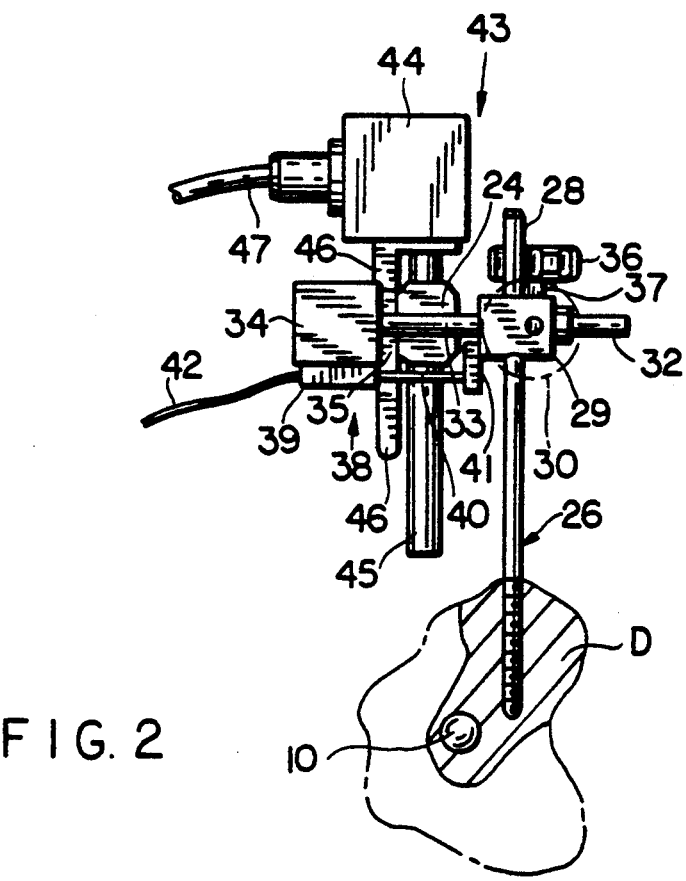
FIG. 2 is a front elevation of a distal feature of the device and bone of FIG. 1.
Figure 3:
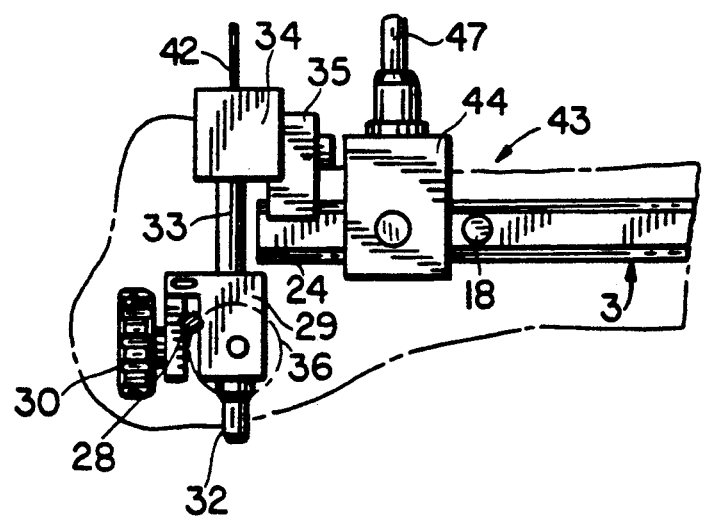
FIG. 3 is a plan view, from above, of the feature of FIG. 2.

With initial reference to FIG. 1, hole-centering means of the invention is generally indicated at 1, in application to a bone having a fracture F between longitudinal ends of the bone, and an intramedullary nail 9 is positioned in the medullary cavity for repair of the fracture F; nail 9 is of metal, preferably stainless steel. The device 1 comprises a frame 2, formed from an elongate template 3 which can be secured in fixed positions to an offsetting arm 4. Arm 4 carries a chuck sleeve 5 having an adjustment grip 6. The chucking end 7 of sleeve 5 includes elements for releasable chucking engagement to the proximal end 8 of the intramedullary nail 9, the distal end of which is indicated at 10. Nail 9 has distal-end holes 11, 12 and proximal-end holes 13, 14 designed to receive transverse bolts (not shown), which can be placed in the cortical or spongy tissue of the bone after the nail has been positioned in the medullary cavity M. Intermediate holes 15, 16 for further stabilization of the stumps close to the fracture may also be provided in nail 9, and the axes of all transverse holes will be understood to be parallel to each other and perpendicular to the axis of nail 9.

Figure 5:
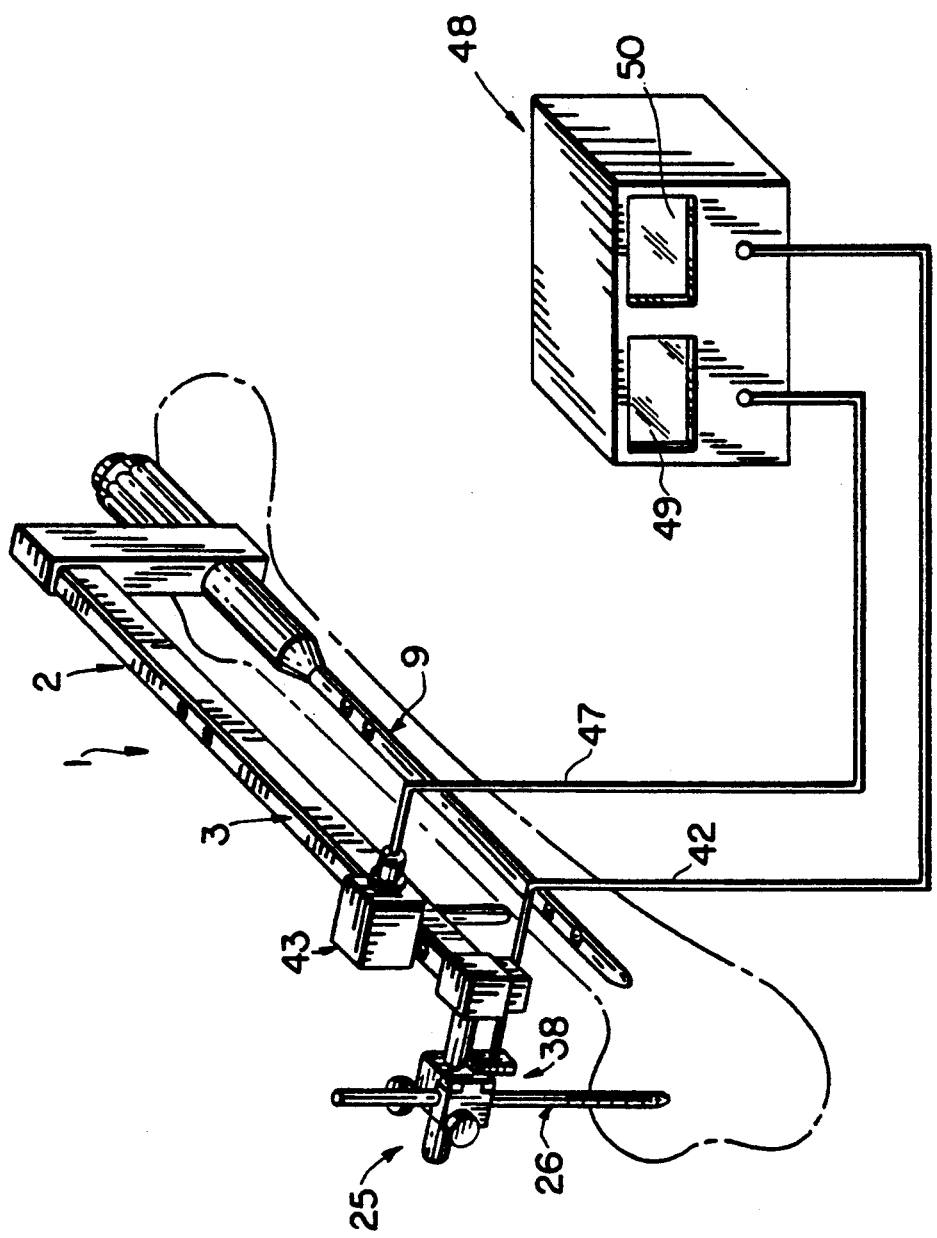
FIG. 5 is a simplified view in perspective to illustrate a control assembly which can be attached to the centering device of FIG. 1.

Transverse passages or guide bores 17, 18, 19, 20, 21, 22 are designed to receive bushes 23 for drilling tools, suggested by dashed lines in FIG. 1 and are provided along the longitudinal length of template 3. Suitably, the distances from transverse member 4 for passages 17, 18, 19, 20, 21, and 22 and for corresponding holes 11, 12, 15, 16, 13, 14 are identical, so that their alignment depends only on the fact that the template 3 and the nail 9 are parallel, although this may vary because of elasticity of the template and its attachment to transverse member 4. An alignment device, which is indicated as a whole by reference number 25 (FIG. 5), is provided to ensure that these two can be adjusted to be parallel, and therefore that the passages in the template are centered on the blind holes in the intramedullary nail.

In particular, the alignment means 25 comprises a stabilizing member which can be anchored at the distal end of the bone, in a longitudinal position beyond the distal end 10 of the intramedullary nail, and the stabilizing member can be secured to the distal end of template 24 by attachment means of adjustable length.

More specifically, the stabilizing member comprises a bar 26 with a threaded end 27 which can be anchored in a distal condyle of the bone and has an exposed or free end 28 which forms a solid reference and abutment member for the distal end 24 of the template.

Figure 4:
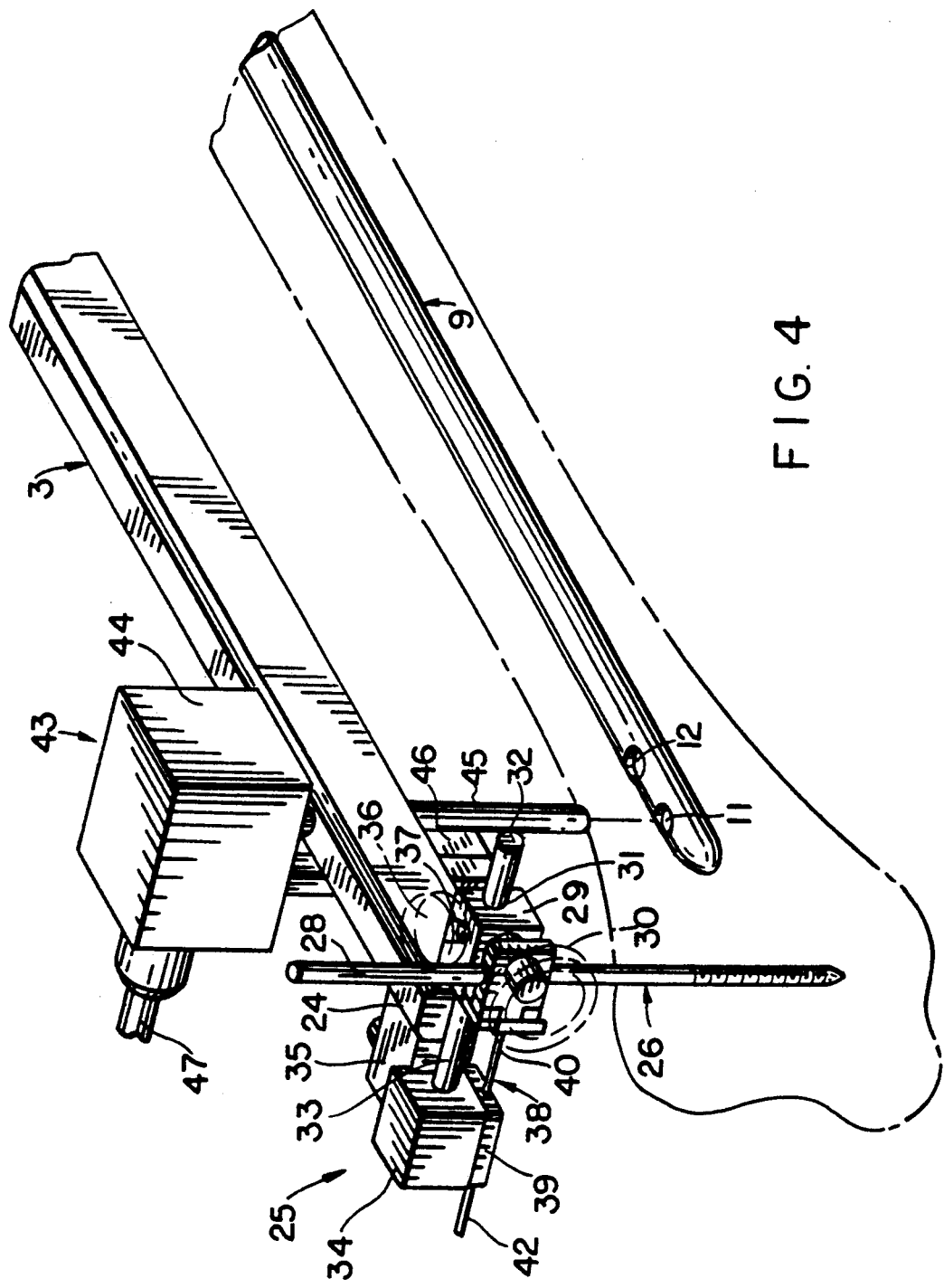
FIG. 4 is a perspective view of the distal feature of FIGS. 2 and 3, on a slightly enlarged scale.

The attachment means of adjustable length comprises transverse guide means which extend between the distal end 24 of the template and stabilizing bar 26. Such guide means may comprise a guide block 29 which can be secured at the free end 28 of bar 26 by means of a screw clamp 30, at the same height as template 3. The block 29 has a guide bore 31 which slidably houses the free end 32 of a transverse rod 33 that is fixed to a supporting block 34; and block 34 is rigidly fixed to the distal end 24 of template 3 by means of a bolted connection 35. A stop or set screw 36 has threaded engagement at 37 (FIG. 4) to slide 29, whereby to lock an adjusted position of rod 33 with respect to block 29; and it will be understood that the functions of guide block 29 and of supporting block 34 can be reversed, without altering the operation of the device. Translational movement of the distal end 24 of the template may be effected manually or by mechanical, electromechanical or other actuating means.

From structure thus far described, it will be seen that the transverse extent of the connection between the distal end 24 of template 3 and the free portion of stabilizing bar 26 can be selectively varied to vary the axial alignment of the template with respect to the intramedullary nail, as viewed in plan and shown diagrammatically in FIGS. 6a, 6b, 6c; this is an adjustment within a geometric plane that is normal to the axis of every hole (11 to 16) in nail 9 and to every guide bore (17 to 22) in template 3. Measurement means are provided to measure in this plane the transverse distance between the distal end of the template and the stabilizing bar 26, thus providing an indirect measurement of the required adjustment to achieve alignment. Such measurement means may consist of an electronic comparator 38, comprising a sensitive member 39 in which a slidable rod 40 having an end plate or foot 41 is spring-urged against the confronting wall of guide block 29. The distance measured by comparator 38 is converted into an electrical signal transmitted via a cable 42.

A metal-detector device, susceptible to the presence of the conductive material of nail 9, and generally indicated by reference number 43, may be advantageously used for the non-invasive determination of template alignment with the intramedullary nail and, therefore, for the alignment of template bore axes at 17, 18 with the corresponding blind distal holes (11, 12) in the intra medullary nail, all without using an X-ray source. Metal-detector device 43 is preferably of the magnetic variety and may be generally as described in U.S. Pat. No. 4,526,177 or in German OS 2,842,203. Specifically, the metal-detector device comprises a head 44 and an elongate cylindrical sensor unit 45 dependent from head 44, which includes electronic components for excitation and detection of signals via sensor 45. Sensor 45 is seen to be sized for accurate mounting via one of the guide passages, e.g., 17, 18 in the distal end 24 of template 3, with orientation toward a corresponding hole 11, 12 in nail 9. Means 43 can be further stabilized in a given position on template 3, by means of a guide bar 46 which is generally L-shaped and is self-stabilizing in flat abutment with a side wall of the template.

When the basic material of the template is present, the metal-detector device detects a specific value for the magnetic field which varies as the sensor axis approaches nail 9 and thus the axis of the hole. The value of the field measured by device 43 and the changes in it are converted into electrical signals which are transmitted via a cable 47.

The signals transmitted by cables 42, 47 are sent to a control center 48 and are displayed on corresponding analog or digital displays at 49, 50.

The procedure for using the described device of the invention is as follows.

After correcting the fracture and after inserting nail 9 into medullary cavity M, the surgeon fixes stabilizing bar 26 in a distal hypophysis of the bone and connects the distal end of template 3 to bar 26. The template is then stably attached to the intramedullary nail, so that the instantaneous directions of the axes of these members can then be adjusted with extreme accuracy. And sensor 45 of the detection means 43 is stably inserted into one of the distal guide passages in the template, e.g., passage 17.

The distal end of template 3 is then moved laterally, in what is effectively a scanning sweep in the geometric plane which is parallel to nail 9 and to which all hole and guide-bore axes are normal. Such movement may be first to the left, as seen in FIG. 6a, namely, to a position A in which guide passage 17 is out of alignment with respect to the corresponding hole 11 in nail 9. In this position, the surgeon records a measurement $d_A$ for the distance measured by electronic comparator 38, as well as the value $F_A$ of the field measured by metal-detector device 43. The surgeon then moves the distal end 24 of template 3 in the opposite direction, i.e., toward the right, as shown in FIG. 6b, to reach position B where the value $F_B$ of the field determined by metal-detector device 43 is $$F_B = F_A \qquad (1)$$

and he records the distance $d_B$ measured by electronic comparator 38. Alignment position C corresponds to distance $d_C$, wherein $$d_C = \tfrac{1}{2}(d_A + d_B) \qquad (2)$$

By moving the distal end until the value $d_C$ measured by comparator 38 is displayed (at 50), passage 17, into which sensor 45 of metal-detector device 43 is inserted, will have been moved into a position which is axially aligned with the corresponding hole 11 in nail 9. Then, by immobilizing shaft 33 on block 29 by means of set screw 37, the surgeon can remove the metal-detector device and insert guide bushes 23 for drilling tools into passages 17, 18, in the certainty of finding corresponding blind holes 11, 12 in nail 9 and accurately drilling the bone for insertion of anchoring bolts.

The means according to the invention may be subjected to many modifications and variants falling within the scope of the invention described in the appended claims. All components may be replaced by their technical equivalents without going beyond the scope of the invention. For example, metal-detector device 43, which is based on the change in the magnetic field when a metal material is present, may be replaced by any device which is based on changes in other force fields, e.g., of an electrical or electromagnetic nature.

What is claimed is:

1. Means for determining the centering alignment of blind holes of an installed intramedullary nail, especially for a bone-surgery operation on a fractured limb, comprising:
   (a) a nail (9) which can be inserted into a medullary cavity (M), which is provided with a distal end (10) and a proximal end (8) and a plurality of spaced transverse holes (11-16) for bone bolts in the proximity of the said ends;
   (b) a frame (2) for supporting the proximal end of the nail from outside the limb, said frame comprising an elongate template (3) having transverse passages (17-22) for drilling tools, and a transverse arm (4) for removable attachment of the nail to said frame;
   (c) means (7) for removably coupling the proximal end (8) of the nail (9) to the transverse arm (4) so that the nail (9) is substantially parallel to the template (3) with its holes (11-16) at the same distance from arm (4) as the corresponding passages (17-22) in the template (3); and
   (d) means (25) for aligning the passages in the template with the holes in the nail by movement of the distal end (24) of the template in a plane which is substantially perpendicular to axes of the passages and the holes, the means of alignment (25) comprising a stabilizing member (26) which can be anchored to the bone beyond the distal end (10) of the nail and which is coupled to the distal end (24) of the template through means of attachment of adjustable length, whereby to selectively position the distal end of the template in said plane and to secure a position of registration as between the distal ends of the template and of the nail.

2. Means according to claim 1, wherein the stabilizing member (26) comprises a partly threaded bar which can be screwed into the bone in the proximity of a distal metaphysis (D) such that its axis is substantially perpendicular to that of the template.

3. Means according to claim 2, wherein said means of attachment of adjustable length comprises guide means (29-34) which extend transversely between the bar (26) and the distal end (24) of the template (3).

4. Means according to claim 3, wherein said guide means comprises a shaft (33) which is substantially perpendicular to the axis of the template (3) and wherein said stabilizing member is a bar (26) slidably mounted within a slide block (29) said shaft (33) and said block (29) being secured to the distal end (24) of the template and the bar (26), respectively, or vice versa, to vary the distance (d) between them.

5. Means according to claim 4, wherein measuring means are provided to determine the distance (d) between the distal end (24) of the template and the stabilizing bar (26).

6. Means according to claim 5, wherein said measurement means comprises an electronic comparator (38) which has a sensitive portion (39) secured to the distal end (24) of the template or to the stabilizing bar (26), and a moving portion (40., 41) which is in contact with the other of the said stabilizing member or said template.

7. Means according to claim 6, wherein the alignment means (25) comprises a metal-detector device (43) capable of determining the strength of a force field in and near a distal hole (11, 12) in the nail which requires centering, said metal-detector device being further capable of determining force-field variations due to misalignment between said hole and a passage (17, 18) in the template (3).

8. Means according to claim 7, wherein the said metal-detector device (43) comprises an orientating sensor (45) which can be inserted into a distal passage (17, 18) in the template (3) in such a way as to be directed toward a corresponding distal hole (11, 12) in the nail.

9. Means according to claim 7, wherein the metal-detector device (43) is of the magnetic type.

10. Means according to claim 7, wherein a control unit (48) is connected to said electronic comparator (38) and/or to said metal-detector device (43) for display of values determined thereby ($d_A$, $d_B$; $F_A$, $F_B$).

11. The method of locating a template guide bore in registry with a blind transverse bolt hole in an intramedullary nail that has been implanted in the medular cavity of a fractured bone, which comprises the steps of:

(a) mounting the template external to the bone and parallel to the intramedullary nail with the proximal end of the template connected to the proximal end of the nail, the axes of the template guide bore and of the transverse bolt hole being parallel and equidistant from said connection and the distal end of the template being movable in a plane perpendicular to said axes;

(b) selecting a metal-detector having a directional axis of force-field response and mounting the same to the template to position the directional axis perpendicular to said plane and in non-invasive proximity to the bone;

(c) moving said distal end in said plane and in a direction which traverses registry with the intramedullary nail, whereby to scan the force field from one to the other side of registry with the nail, whereby to sense a force-field anomaly upon scanned swept traverse of the nail; and (d) determining the center of symmetry of the force-field anomaly, thereby identifying the location of template guide-bore registry with the blind hole in the intramedullary nail.

12. The method of claim 11, in which (e) a stabilizing reference is established to a part of the bone which is distal to the distal end of the intramedullary nail, and (f) the distal end of the template is clamped to the stabilizing reference for that template position which corresponds to the center of symmetry determined by step (d).

13. The method of claim 11, in which the intramedullary nail is of stainless steel, and in which the metal-detector is of the variety which will sense a magnetic-field anomaly encountered in the course of the movement of step (c).

14. The method of locating a template guide bore in registry with a blind transverse bolt hole in an intramedullary nail that has been implanted in the medular cavity of a fractured bone, which comprises the steps of:

(a) mounting the template external to the bone and parallel to the intramedullary nail with the proximal end of the template connected to the proximal end of the nail, with the axes of the template guide bore and of the transverse bolt hole parallel and equidistant from said connection and the distal end of the template being movable in a plane perpendicular to said axes;

(b) establishing a stabilizing reference to a part of the bone which is distal to the distal end of the nail;

(c) selecting a metal-detector and mounting the same to establish a force field embracing that part of the nail which is characterized by the bolt hole;

(d) moving said distal end in said plane and to one side of the distal end of the nail to a first location of predetermined metal-detector output;

(e) measuring in said plane the distance of the distal end of the template from the stabilizing reference of step (b);

(f) moving the distal end of the template in said plane and to the other side of the distal end of the nail and to a second location at which the same predetermined metal-detector output is noted;

(g) measuring in said plane the distance of the distal end of the template from the stabilizing reference of step (b);

(h) calculating from the measurements of steps (e) and (g) the half-way point of the sum of said measurements; and (i) clamping the distal end of the template to the stabilizing reference for a setting of the distal end of the template at the half-way point calculated by step (h).

15. The method of claim 14, in which the intramedullary nail is of stainless steel, and in which the metal-detector is of the variety which generates a magnetic field having a directional axis of magnetic-field response which is perpendicular to said plane and in non-invasive proximity to the bone, and in which the metal-detector produces an electrical-signal output which varies in accordance with nail location in said field.

* * * * *